United States Patent
Manzel et al.

(10) Patent No.: US 11,213,867 B2
(45) Date of Patent: Jan. 4, 2022

(54) METHOD FOR CLEANING PHOSGENE CONDUCTING APPARATUS

(71) Applicant: Covestro Deutschland AG, Leverkusen (DE)

(72) Inventors: Dirk Manzel, Moers (DE); Peter Plathen, Krefeld (DE); Peter Wolf, Duisburg (DE); Udo Boegel, Duisburg (DE)

(73) Assignee: Covestro Deutschland AG, Leverkusen (DE)

( * ) Notice: Subject to any disclaimer, the term of this patent is extended or adjusted under 35 U.S.C. 154(b) by 193 days.

(21) Appl. No.: 16/640,243

(22) PCT Filed: Sep. 3, 2018

(86) PCT No.: PCT/EP2018/073629
§ 371 (c)(1),
(2) Date: Feb. 19, 2020

(87) PCT Pub. No.: WO2019/048386
PCT Pub. Date: Mar. 14, 2019

(65) Prior Publication Data
US 2020/0246845 A1    Aug. 6, 2020

(30) Foreign Application Priority Data

Sep. 6, 2017 (EP) .................... 17189560

(51) Int. Cl.
| | | |
|---|---|---|
| *B08B 9/032* | (2006.01) | |
| *B08B 5/00* | (2006.01) | |
| *C11D 7/04* | (2006.01) | |
| *C11D 11/00* | (2006.01) | |
| *C01B 32/80* | (2017.01) | |
| *B01D 53/02* | (2006.01) | |
| *B01J 19/00* | (2006.01) | |

(52) U.S. Cl.
CPC ............ *B08B 9/0328* (2013.01); *B01D 53/02* (2013.01); *B01J 19/0006* (2013.01); *B08B 5/00* (2013.01); *C01B 32/80* (2017.08); *C11D 11/0041* (2013.01); *B01D 2253/102* (2013.01); *B01D 2259/40084* (2013.01); *B01J 2219/00247* (2013.01)

(58) Field of Classification Search
None
See application file for complete search history.

(56) References Cited

U.S. PATENT DOCUMENTS 4,064,218 A    12/1977 Scholz et al.

FOREIGN PATENT DOCUMENTS

| EP | 3243563 A1 | 11/2017 |
|---|---|---|
| WO | 2015144462 A1 | 10/2015 |
| WO | 2016109987 A1 | 7/2016 |

OTHER PUBLICATIONS

"Phosgene Safety Practices for design, production and processing", International Isocyanate Institute Inc., 2012 edition, part 2, point 3.2.3, 11 pages.
"Phosgene Safe Practice Guidelines", American Chemical Council, 2014 version in chapter 9.0 ("Equipment Cleaning and Repair"), 7 pages.
International Search Report, PCT/EP2018/073629, dated Nov. 13, 2018, Authorized officer: Wolfgang Fitz, 4 pages.

*Primary Examiner* — Eric W Golightly
*Assistant Examiner* — Arlyn I Rivera-Cordero
(74) *Attorney, Agent, or Firm* — Donald R. Palladino

(57) ABSTRACT

The invention relates to a method for cleaning a phosgene conducting apparatus, comprising: washing the apparatus with hot inert gas, followed by washing the apparatus with cold inert gas; conveying gaseous ammonia for breaking down phosgene residues with a continuous increase in temperature until a maximum temperature ranging between 30° C. to 120° C. is reached; once the maximum temperature is reached, shutting down the ammonia supply and the conveying of inert gas, optionally followed by washing the apparatus with an aqueous stream.

15 Claims, No Drawings

METHOD FOR CLEANING PHOSGENE CONDUCTING APPARATUS

CROSS-REFERENCE TO RELATED APPLICATION

This application is a national stage application under 35 U.S.C. § 371 of PCT/EP2018/073629, filed Sep. 3, 2018, which claims the benefit of European Application No. 17189560.0, filed Sep. 6, 2017, both of which are incorporated by reference herein.

FIELD

The invention relates to a process for cleaning a phosgene-conducting apparatus, comprising a purge of the apparatus with hot inert gas, followed by a purge of the apparatus with cold inert gas, passage of gaseous ammonia for breakdown of phosgene residues with continuously rising temperature until a temperature maximum in the range from 30° C. to 120° C. is attained, after attainment of the temperature maximum stoppage of the ammonia supply and passage of inert gas, optionally (and preferably) followed by a purge of the apparatus with an aqueous stream.

BACKGROUND

Phosgene finds use in many fields of chemistry, whether as an auxiliary or as intermediate. The most important field of use in terms of volume is the preparation of di- and/or polyisocyanates as starting materials for polyurethane chemistry. Particular mention should be made here of tolylene diisocyanate (especially meta-tolylene diisocyanate), naphthalene diisocyanate (especially naphthalene 1,5-diisocyanate), pentane 1,5-diisocyanate, hexamethylene 1,6-diisocyanate, isophorone diisocyanate, diisocyanatodicyclohexylmethane, xylylene diisocyanate (especially xylylene 1,3- and/or 1,4-diisocyanate) and the di- and polyamines of the diphenylmethane series. A further important field of use for the use of phosgene is the preparation of polycarbonates.

The production plants for preparation of such substances naturally include numerous phosgene-conducting apparatuses, for example reactors for phosgene preparation or reactors for reaction of phosgene with appropriate reactive starting material such as amines or phenols. Furthermore, numerous workup apparatuses such as distillation columns should be regarded as phosgene-conducting apparatuses. The same is of course also applicable to numerous peripheral units such as tanks and pipelines.

In all cases, it may be necessary to open such apparatuses, for example for maintenance, repair and cleaning operations or in order to remove spent catalyst, for example, from a reactor. Because of the high toxicity of phosgene, it is has already been good industrial practice for many decades to very carefully free such apparatuses of phosgene prior to opening. Instructions that are common practice in industry for this purpose are known to the person skilled in the art. Reference is made by way of example to "*Phosgene Safety Practices for design, production and processing*" from International Isocyanate Institute Inc. In the 2012 edition, a procedure is described therein in part 2 under point 3.2.3 that includes the purging of the apparatus with nitrogen, the purging of the apparatus with ammonia, and the flooding of the apparatus with water, sodium hydroxide solution or aqueous ammonia. Reference is likewise made to the "*Phosgene Safe Practice Guidelines*" from the American Chemical Council. It is disclosed therein, in the 2014 version in chapter 9.0 ("*Equipment Cleaning and Repair*"), that it is possible to free apparatuses that are difficult to clean of phosgene with aqueous ammonia inter alia.

Phosgene is typically prepared by reaction of carbon monoxide and chlorine over an activated carbon catalyst. Before a reactor used for the purpose can be opened, it has to be ensured that the activated carbon present therein has also been freed of phosgene, which must be conducted very carefully owing to its high internal surface area. This objective is addressed by international patent application WO 2016/109987 A1, which is directed to a process for rapid freeing of a phosgene production column of phosgene. This process comprises, after stopping the feed of the carbon monoxide and chlorine starting materials, first a step A) of purging with nitrogen in order to drive the majority of phosgene out of the reactor. This is optionally followed by a step B) in which ammonia gas is guided into the phosgene production column (the outlet orifice of which is now closed) until a pressure in the range from 0.11 MPa to 5 MPa is established. After 1 hour to 10 hours, the system is decompressed by opening the outlet orifice of the phosgene production column. This operation of injecting ammonia and decompressing is repeated several times if required. This is firstly intended to prevent the blockage of the downstream piping and secondly to achieve depletion of phosgene present in the pores of the activated carbon catalyst as well. This optional step B) is followed by a step C) of passing ammonia gas through the phosgene production column. This step is conducted until the phosgene content measured in the outlet of the phosgene production column drops to a value of not more than 1 ppm. The success of the phosgene breakdown is thus accordingly verified only by the analysis of the residual phosgene content. The application further discloses, in the case of use of a shell and tube reactor for phosgene production, the cleaning of the reactor with water after removal of the activated carbon.

However, the verification of the success of the phosgene breakdown solely via sampling and analysis of the residual phosgene content on breakdown of the phosgene with gaseous ammonia only is not uncritical since it cannot be ruled out that hidden "phosgene clusters" will be missed by this method. Such "phosgene clusters" can occur especially in shell and tube reactors for phosgene production if tubes are blocked by caking of catalyst particles.

There was therefore a need for further improvements in the field of cleaning, i.e. especially the freeing from phosgene, of phosgene-conducting apparatuses. It would especially be desirable to be able to find out in a simple manner when the cleaning operation, i.e. the breakdown of residual phosgene in particular, is complete and the apparatus can be opened without risk. More particularly, it would be desirable to further improve phosgene breakdown with gaseous ammonia, which is attractive per se.

SUMMARY

Taking account of this requirement, the present invention provides a process for cleaning a phosgene-conducting apparatus, comprising the steps of:
a) providing a device for gas removal from the apparatus to be cleaned and a device for gas supply to the apparatus to be cleaned and shutting off all conduits that may additionally be connected to the apparatus to be cleaned;
b) passing an inert gas, especially passing nitrogen, having a temperature in the range from 100° C. to 500° C., preferably in the range from 120° C. to 400° C., more preferably in the range from 150° C. to 350° C., most preferably in the range from 250° C. to 300° C., through the apparatus to be cleaned, especially at a pressure in the apparatus to be cleaned below ambient pressure, preferably at a pressure in the range from 10 mbar to 1000 mbar, more preferably in the range from 100 mbar to 990 mbar, most preferably in the range from 500 mbar to 980 mbar, where step b) is additionally especially conducted until the proportion by volume of phosgene, determined continuously or at intervals of up to 300 h, preferably at intervals in the range from 50 h to 300 h, more preferably from 60 h to 200 h, even more preferably from 70 h to 150 h and very exceptionally preferably from 80 h to 120 h, in the inert gas removed from the apparatus to be cleaned by color change as a result of the reaction of phosgene with ethylaniline and dimethylaminobenzaldehyde within the temperature range from 10° C. to 30° C., based on the total volume of the gas stream that flows through the at least one outlet per unit time, drops to a value of not more than 1 ppm;

c) stopping the (hot) inert gas stream from step b), followed by the cooling of the apparatus to be cleaned to a previously defined temperature, measured in the device for gas removal, in the range from 0° C. to 70° C., preferably in the range from 10° C. to 60° C., more preferably in the range from 20° C. to 50° C., most preferably in the range from 30° C. to 40° C., by passing through an inert gas, especially nitrogen, having a temperature equal to or below the previously defined temperature, where the inert gas stream from step c) may additionally also be maintained even after cooling of the apparatus to be cleaned;

d) once the apparatus to be cleaned has been cooled in step c), passing through gaseous ammonia from an ammonia gas source, especially by feeding into the maintained inert gas stream from step c), to obtain an ammonia-containing gas mixture, where the flow rate of the gaseous ammonia is chosen such that the temperature in the gas mixture removed from the apparatus to be cleaned rises continuously and drops again after reaching a maximum, where the temperature maximum is in the range from 30° C. to 120° C., preferably in the range from 50° C. to 110° C., more preferably in the range from 60° C. to 100° C. and most preferably in the range from 70° C. to 90° C.;

e) no earlier than after attainment of the temperature maximum in step d), removing the ammonia gas source from the apparatus to be cleaned, followed by passing of an inert gas through the apparatus to be cleaned, especially by further maintaining the inert gas stream from step c);

f) optionally, after stopping the inert gas stream, providing a liquid inlet into the apparatus to be cleaned and a liquid outlet out of the apparatus to be cleaned and passing an aqueous stream, especially water, through the apparatus to be cleaned, especially at least until the pH of the aqueous stream exiting from the apparatus is in the range from 7.0 to 10.0, preferably from 7.0 to 9.0, more preferably from 7.0 to 8.0.

DETAILED DESCRIPTION

"Phosgene-conducting apparatuses" in the context of the invention are all plant components that can come into contact with phosgene in operation, i.e. especially reactors for phosgene production, reactors for reaction of phosgene with a reactive starting material, workup apparatuses for purification of products that have been produced using phosgene (especially distillation columns), and peripheral units such as pipelines and vessels (e.g. tank vessels).

There firstly follows a brief summary of various possible embodiments of the invention:

In a first embodiment of the invention, which may be combined with all other embodiments, step b) is performed at a pressure below ambient pressure.

In a second embodiment of the invention, which is a particular configuration of the first embodiment, the pressure in step b) is in the range from 10 mbar to 1000 mbar, preferably in the range from 100 mbar to 990 mbar, more preferably in the range from 500 mbar to 980 mbar.

In a third embodiment of the invention, which can be combined with all other embodiments, step b) is conducted until the proportion by volume of phosgene, determined continuously or at intervals of up to 300 h, preferably at intervals in the range from 50 h to 300 h, more preferably from 60 h to 200 h, even more preferably from 70 h to 150 h and very exceptionally preferably from 80 h to 120 h, in the inert gas removed from the apparatus to be cleaned by color change as a result of the reaction of phosgene with ethylaniline and dimethylaminobenzaldehyde within the temperature range from 10° C. to 30° C., based on the total volume of the gas stream that flows through the at least one outlet per unit time, drops to a value of not more than 1 ppm.

In a fourth embodiment of the invention, which can be combined with all other embodiments, the previously defined temperature from step c) measured in the device for gas removal is in the range from 10° C. to 60° C., preferably in the range from 20° C. to 50° C., more preferably in the range from 30° C. to 40° C.

In a fifth embodiment of the invention, which can be combined with all other embodiments, the inert gas stream from step c) is still maintained after completion of cooling of the apparatus to be cleaned.

In a sixth embodiment of the invention, which is a particular configuration of the fifth embodiment, the gaseous ammonia from an ammonia gas source is passed through in step d) by feeding it into the maintained inert gas stream from step c).

In a seventh embodiment of the invention, which is a particular configuration of the fifth and sixth embodiments, the passage of an inert gas through the apparatus to be cleaned in step e) is brought about solely by maintaining the inert gas stream from step c).

In an eighth embodiment of the invention, which is combinable with all other embodiments, step f) is conducted, and the aqueous stream is guided through the apparatus to be cleaned at least until the pH of the aqueous stream exiting from the apparatus is in the range from 7.0 to 10.0, preferably from 7.0 to 9.0, more preferably from 7.0 to 8.0.

In a ninth embodiment of the invention, which is combinable with all other embodiments, the apparatus to be cleaned is (i) an activated carbon-filled reactor suitable for preparing phosgene from carbon monoxide and chlorine, or (ii) an activated carbon-filled reactor suitable for absorbing or decomposing phosgene in phosgene-containing gas streams, where the flow rate of gaseous ammonia which is guided through the activated carbon-filled reactor in step d) is in the range from 3 L/h to 30 L/h per metric ton of activated carbon.

In a tenth embodiment of the invention, which is combinable with all other embodiments, the apparatus to be cleaned is an activated carbon-filled reactor suitable for preparation of phosgene from carbon monoxide and chlorine.

In an eleventh embodiment of the invention, which is a particular configuration of the tenth embodiment, the activated carbon-filled reactor suitable for preparation of phosgene from carbon monoxide and chlorine is part of a production plant for preparation of a chemical product by reaction of a phosgene-reactive starting material with phosgene.

In a twelfth embodiment of the invention, which is a particular configuration of the tenth and eleventh embodiment, the phosgene-reactive starting material is a compound having two or more phenolic hydroxyl groups or a compound having two or more primary amino groups.

In a thirteenth embodiment of the invention, which is a particular configuration of the eleventh and twelfth embodiment, the production plant for preparation of a chemical product has n independently controllable, activated carbon-filled reactors suitable for preparation of phosgene from carbon monoxide and chlorine, where n is a natural number from 2 to 5, where phosgene is prepared from carbon monoxide and chlorine in m reactors, where m is a natural number in the range from 1 to n−1, where cleaning steps a) to e) and optionally f) are conducted in at least one reactor.

In a fourteenth embodiment of the invention, which is a particular configuration of the ninth, tenth, eleventh, twelfth and thirteenth embodiment, step e) or, if conducted, step f) is followed by removing the activated carbon and replacing it with fresh activated carbon.

In a fifteenth embodiment of the invention, which is combinable with all other embodiments, the inert gas used in all steps in which the use of an inert gas is envisaged is nitrogen.

The embodiments briefly outlined above and further possible configurations of the invention are elucidated in detail hereinafter. Various embodiments are combinable with one another as desired unless the opposite is clearly apparent to the person skilled in the art from the context.

Prior to the performance of the process of the invention, the supply of the starting materials normally introduced into the apparatus to be cleaned (i.e. carbon monoxide and chlorine in the case of a phosgene production reactor, amine and phosgene in the case of a reactor for phosgenation of isocyanates, etc.) should obviously be stopped and, if required, any liquid level present (for example of reaction solution) should be drained.

In step a) of the process of the invention, the apparatus to be cleaned is then prepared for the further steps. For this purpose, a device for gas supply and the means of gas removal are provided. This can be accomplished, for example, by fitting appropriate conduits to flanges present that are closed in regular operation or by opening fixedly installed gas supply and gas removal conduits that are closed in the regular operation of the apparatus to be cleaned by devices such as valves. The procedure of the invention of the "providing of a device for gas removal from the apparatus to be cleaned and for gas supply to the apparatus to be cleaned" does of course also include configurations in which two or more gas inlets and/or two or more gas outlets are provided.

In addition, all conduits present beyond that (such as conduits for the supply and removal of the substances present in regular operation in the apparatus to be cleaned) are shut off. The term "shutting off" in this connection includes both the closing of conduits by corresponding devices such as valves and the complete severing of conduits and closing of the resultant orifices.

In step b), a hot inert gas stream is then guided through the apparatus to be cleaned. A suitable inert gas is especially nitrogen, carbon dioxide or a noble gas such as argon or helium. Preference is given to using nitrogen. The hot inert gas stream is introduced through the device for gas supply provided in step a) and removed through the device for gas removal provided in step a). This step serves to drive out the majority of the phosgene present in the apparatus to be cleaned. The device for gas removal is preferably connected to an offgas workup comprising an apparatus for phosgene breakdown (especially by catalytic breakdown over activated carbon in the presence of water).

The hot inert gas has a temperature in the range from 100° C. to 500° C., preferably in the range from 120° C. to 400° C., more preferably in the range from 150° C. to 350° C. and most preferably in the range from 250° C. to 300° C. The effect of the high temperature is that any liquid phosgene present in the apparatus to be cleaned evaporates and is driven out in gaseous form. The temperature of the inert gas stream is appropriately measured online with temperature sensors known to those skilled in the art.

In a preferred embodiment, step b) is performed at reduced pressure (below ambient pressure), which likewise facilitates the driving-out of phosgene. The pressure is preferably in the range from 10 mbar to 1000 mbar, more preferably in the range from 100 mbar to 990 mbar, most preferably in the range from 500 mbar to 980 mbar. For this purpose, a vacuum-generating pump or, in pressure ranges below 500 mbar, a ventilator is used.

Preference is given to measuring the phosgene content (proportion by volume of phosgene) in the inert gas stream that exits from the apparatus to be cleaned with the gas removal device. This is done either continuously or at intervals. In the latter case, measurements are made at least once every 300 h. Preference is given to measuring at intervals in the range from 50 h to 300 h, more preferably from 60 h to 200 h, even more preferably from 70 h to 150 h and very exceptionally preferably from 80 h to 120 h. This measurement can in principle be effected by any phosgene detection methods known to the person skilled in the art which typically give results that are comparable within the scope of insignificant measurement inaccuracies. In the case of doubt, for the purposes of the present invention, the value determined by color change owing to the reaction of phosgene with ethylaniline and dimethylaminobenzaldehyde within the temperature range from 10° C. to 30° C. is crucial. For this purpose, for example, the company Dräger supplies suitable measurement devices (such as the "Dräger tube", "CH19 401"). More particularly, once the measured phosgene content has fallen to a value of not more than 1 ppm, the next step can be commenced.

In step c) of the process of the invention, the hot inert gas stream from step b) is shut down and the apparatus to be cleaned is cooled down, specifically to a temperature (previously defined) in the range from 0° C. to 70° C., preferably in the range from 10° C. to 60° C., more preferably in the range from 20° C. to 50° C., most preferably in the range from 30° C. to 40° C. This cooling is effected by passing through a comparatively cold inert gas stream, namely by passing through an inert gas stream having a temperature equal to or below the previously defined temperature. Suitable inert gases are the same as for step b). The comparatively cold inert gas stream is introduced through the device for gas supply provided in step a) and removed through the device for gas removal provided in step a). The cooling can also be implemented by no longer heating the inert gas stream from step b) (or no longer to the extent as in step b)), such that its temperature falls gradually. In this embodiment, a fluid transition from step b) to step c) takes place, and the "shutdown" of the hot inert gas stream from step b) then simply means lowering of its temperature to a smaller value than required as a minimum in step b), i.e. to a value below 100° C. (or, in preferred embodiments, below 120° C. or below 150° C. or below 250° C.). The success of the cooling of the apparatus to be cleaned is appropriately verified by measuring the temperature of the inert gas stream exiting from the device for gas removal.

The comparatively cold inert gas stream from step c) is preferably maintained even after cooling of the apparatus to be cleaned.

In step d) of the process of the invention, gaseous ammonia from an ammonia gas source is guided through the apparatus to be cleaned. The ammonia gas source may be any device known in principle to the person skilled in the art for providing gaseous ammonia. Preference is given to using a pressure vessel in which dry ammonia is in liquefied form under elevated pressure relative to ambient pressure (preferably at a pressure in the range from 5 $bar_{(g)}$ to 15 $bar_{(g)}$). In this embodiment, the liquid ammonia is introduced from the pressure vessel into the device for gas supply provided in step a), where the ammonia evaporates spontaneously as a result of expansion. The ammonia or ammonia-containing gas mixture is led off from the apparatus to be cleaned by the device for gas removal provided in step a).

In a preferred configuration, the feeding of the ammonia is accomplished by feeding the ammonia gas stream into the inert gas stream from step c) (that has been maintained in this embodiment). The associated dilution of the ammonia has the advantage that the formation of local hotspots is avoided. An ammonia-containing gas mixture (mixture of ammonia and inert gas) is obtained here. The flow rate of the gaseous ammonia is chosen here such that the temperature in the ammonia-containing gas mixture removed from the apparatus to be cleaned rises continuously. This rise in temperature is attributable to the exothermicity of the reaction of phosgene with ammonia; the concentration of the ammonia fed in in the inert gas stream must be sufficiently high to assure that the breakdown reaction proceeds with sufficient speed and a sufficient temperature rise. The proportion by volume of the gaseous ammonia fed in in step d) is therefore preferably from 0.01% to 0.1%, based on the total volume of inert gas stream and ammonia fed in. The required flow rate of the gaseous ammonia fed in in step d) can be easily ascertained by the person skilled in the art by simple preliminary experiments. If the apparatus to be cleaned is an activated carbon-charged reactor, for example a reactor for production of phosgene or a reactor for absorption or breakdown of phosgene in phosgene-containing gas streams, preference is given to using 3 L/h to 30 L/h of ammonia per metric ton of activated carbon in the apparatus to be cleaned. In these cases, the process of the invention especially serves to free such a reactor of phosgene residues (that may even be in the activated carbon itself) prior to the exchange of the activated carbon present in the reactor for fresh activated carbon. The volume flow rate unit "L/h" here relates to the volume of gaseous ammonia actually present under the given conditions of pressure and temperature, which can be determined easily with flowmeters known to the person skilled in the art, for example a rotameter.

As a result of the exothermic breakdown reaction in step d), the temperature at first rises continuously. After breakdown of the phosgene present, the temperature drops again; a temperature maximum is thus passed through. This is in the range from 30° C. to 120° C., preferably in the range from 50° C. to 110° C., more preferably in the range from 60° C. to 100° C. and most preferably in the range from 70° C. to 90° C. Once this temperature maximum has been passed through, the ammonia gas supply can be shut down. To increase safety, it may be appropriate to maintain the ammonia gas supply in step d) also for a period of 1 h to 8 h after attainment of the temperature maximum.

In step e), the ammonia gas source is separated from the apparatus to be cleaned and an inert gas stream is guided through the apparatus to be cleaned. In the preferred embodiment already mentioned above, this is accomplished in a simple manner by further maintaining the inert gas stream from step c). The inert gas supply from step e) is preferably maintained for a period of 1 minute to 2 h.

In many cases, the apparatus to be cleaned has already been sufficiently freed of phosgene after the performance of step e) in order to be opened, for example for maintenance, repair and cleaning operations. In cases of particularly persistent phosgene contamination, it may be necessary to add a further cleaning step.

In this optional step f), the apparatus to be cleaned is purged with an aqueous stream. For this purpose, a liquid inlet into and a liquid outlet out of the apparatus to be cleaned are first provided.

This can be accomplished, for example, by fitting appropriate conduits to flanges present that are closed in regular operation or by opening fixedly installed liquid inlets and liquid outlets that are closed in the regular operation of the apparatus to be cleaned by devices such as valves or are utilized for other purposes. The procedure of the invention of the "providing of a liquid inlet into the and a liquid outlet out of the apparatus to be cleaned" does of course also include configurations in which two or more liquid inlets and/or two or more liquid outlets are provided.

Suitable "aqueous streams" in step d) are water qualities such as distilled water, demineralized water, water from the available supply grid, steam condensate (steam condensed in heat exchangers) and aqueous process streams (aqueous streams that are obtained in chemical production, provided that they are not acidic because this would promote corrosion).

When step d) is conducted, the passage of the aqueous stream is especially maintained at least until the pH of the aqueous stream exiting from the apparatus is in the range from 7.0 to 10.0, preferably from 7.0 to 9.0, more preferably from 7.0 to 8.0. In the context of the present invention, pH values relate to a temperature of 30° C. The effect of this is that the apparatus is not exposed to any acidic, corrosive media.

The process of the invention is particularly suitable for cleaning of an activated carbon-filled reactor for production of phosgene from carbon monoxide and chlorine. Such reactors are used especially as a constituent of production plants for production of chemical products by reaction of phosgene-reactive starting materials with phosgene. Suitable phosgene-reactive starting materials are especially compounds having two or more phenolic hydroxyl groups (to form polycarbonates) and compounds having two or more primary amine groups (to form polyisocyanates).

In a preferred embodiment of the invention, the production plant for preparation of the chemical product has n independently controllable, activated carbon-filled reactors for preparation of phosgene from carbon monoxide and chlorine, where n is a natural number from 2 to 5, where phosgene is prepared from carbon monoxide and chlorine in m reactors, where m is a natural number in the range from 1 to n−1, where cleaning steps a) to e) and optionally f) are conducted in at least one reactor. In this manner, it is possible to change the activated carbon catalyst in one of the phosgene production reactors without having to interrupt the operation of the other phosgene production reactors.

The process of the invention accordingly enables a particularly advantageous configuration of the catalyst change in a phosgene production reactor. Such a catalyst change is performed by, after step e) or, if conducted, after step f), removing the activated carbon and replacing it with fresh activated carbon in a step g).

Overall, the process of the invention features at least the following advantages:
(i) Simple monitoring of the progression of phosgene breakdown reaction via the temperature.
(ii) Since the juncture of the breakdown of phosgene is recognized immediately, the repair or other maintenance measures can be started immediately, and time delays that would have resulted in product loss are avoided.
(iii) The phosgene breakdown reaction is performed in a neutral to alkaline medium, which protects the metallic equipment from a possible acid attack.
(iv) In the preferred embodiment with maintenance of the inert gas stream in step d), as a result of the dilution of the ammonia with nitrogen brought about thereby, the formation of "hotspots" ("runaway" of the reaction) is avoided. The dilution leads to a homogeneous distribution of ammonia and hence to a uniform rise of the exothermic reaction.

EXAMPLES

Example 1 (Comparative Example): Activated Carbon Change in a Phosgene Generator without the Aid of Ammonia A phosgene generator having a capacity of 12 m$^3$ was provided with a nitrogen supply and connected to the offgas system of the production plant. The remaining inlets and outlets of the phosgene generator were closed. Then 120 m$^3$ (STP)/h of nitrogen having a temperature of 280° C. were passed through the phosgene generator by the nitrogen supply while maintaining the jacket heating of the phosgene generator for 21 days. At the same time, by means of a ventilator installed in the offgas system of the production plant, the pressure at the exit from the phosgene generator was lowered to 980 mbar (absolute). After this operation, a phosgene content of <1 ppm was measured by means of a "Dräger tube" CH19 401 at standard pressure in the exit from the apparatus. Then the jacket heating was closed and the nitrogen supply was shut down. The phosgene generator was lastly purged with 1000 L/h of steam condensate. At the start, the exiting purge condensate had a pH of 2. After purging for two days, a pH of 6.7 had been established gradually, and the purging was ended. After the discharge of the purge condensate, the activated carbon was sucked out of the phosgene generator within one day. The whole process takes 23 days. The inspection of the phosgene generator found slight metal erosion resulting from acid attack.

Example 2 (Inventive): Activated Carbon Change in a Phosgene Generator Using Gaseous Ammonia A phosgene generator having a capacity of 12 m$^3$ was provided with a nitrogen supply and connected to the offgas system of the production plant. The remaining inlets and outlets of the phosgene generator were closed (step a)). Then 120 m$^3$ (STP)/h of nitrogen having a temperature of 280° C. were passed through the phosgene generator by the nitrogen supply while maintaining the jacket heating of the phosgene generator for 7 days. At the same time, by means of a ventilator installed in the offgas system of the production plant, the pressure at the exit from the phosgene generator was lowered to 980 mbar (absolute). After this operation, a phosgene content of <1 ppm was measured by means of a "Dräger tube" CH19 401 at standard pressure in the exit from the apparatus (step b)). Then the jacket heating was closed. Thereafter, the apparatus was purged with nitrogen having a temperature of 25° C. for 1 day and subsequently had a temperature in the gas exit of 30° C. (step c)). The cold nitrogen continued to run at 120 m$^3$ (STP)/h, and 50 L/h of ammonia gas, which was taken as dry ammonia from a pressure vessel at 10 bar$_{(g)}$, was metered via a needle valve (corner valve regulator from Hofer) into the cold nitrogen stream (step d)). The temperature in the exit from the phosgene combiner rose from 30° C. to 80° C. within 10 hours. In the next hour, the temperature remained constant and then dropped. Then the supply of ammonia gas was shut down, and purging was effected with cold nitrogen (120 m$^3$ (STP)/h, 25° C.) for a further 2 hours (step e)). Then the nitrogen supply was shut down. The phosgene generator was lastly purged with 1000 L/h of steam condensate having a temperature of 28° C. until a pH of 7.8 had been established, which took one day (step f)). The wash water was supplied continuously as obtained via a gravitational separator to the wastewater treatment in a water treatment plant. After the discharge of the wash water, the activated carbon was sucked out of the phosgene generator within one day. The activated carbon sucked out was incinerated in an incineration plant. The whole process takes 11 days. The inspection of the phosgene generator did not find any metal erosion.

The invention claimed is:

1. A process for cleaning a phosgene-conducting apparatus, comprising:
   a) providing a device for gas removal from the apparatus to be cleaned and a device for gas supply to the apparatus to be cleaned and shutting off all conduits that may additionally be connected to the apparatus to be cleaned;
   b) passing an inert gas having a temperature in the range from 100° C. to 500° C. through the apparatus to be cleaned;
   c) stopping the inert gas stream from step b), followed by the cooling of the apparatus to be cleaned to a previously defined temperature, measured in the device for gas removal, in the range from 0° C. to 70° C. by passing through an inert gas having a temperature equal to or below the previously defined temperature;
   d) once the apparatus to be cleaned has been cooled in step c), passing through gaseous ammonia from an ammonia gas source to obtain an ammonia-containing gas mixture, where the flow rate of the gaseous ammonia is chosen such that the temperature in the gas mixture removed from the apparatus to be cleaned rises continuously and drops again after reaching a maximum temperature, wherein the maximum temperature is in the range from 30° C. to 120° C.;
   e) no earlier than after attainment of the maximum temperature in step d), removing the ammonia gas source from the apparatus to be cleaned, followed by passing of an inert gas through the apparatus to be cleaned; and
   f) after stopping the inert gas stream, providing a liquid inlet into the apparatus to be cleaned and a liquid outlet out of the apparatus to be cleaned and passing an aqueous stream through the apparatus to be cleaned.

2. The process as claimed in claim 1, in which step b) is conducted until the proportion by volume of phosgene, determined continuously or at intervals of up to 300 h in the inert gas removed from the apparatus to be cleaned by color change as a result of the reaction of phosgene with ethylaniline and dimethylaminobenzaldehyde within the temperature range from 10° C. to 30° C., based on the total volume of the gas stream that flows through the at least one outlet per unit time, drops to a value of not more than 1 ppm.

3. The process as claimed in claim 1, in which the previously defined temperature from step c), measured in the device for gas removal, is in the range from 10° C. to 60° C.

4. The process as claimed in claim 1, in which the aqueous stream is guided through the apparatus to be cleaned at least until the pH of the aqueous stream exiting from the apparatus is in the range from 7.0 to 10.0.

5. The process as claimed in claim 1, in which step b) is conducted at a pressure below ambient pressure.

6. The process as claimed in claim 5, in which the pressure in step b) is in the range from 10 mbar to 1000 mbar.

7. The process as claimed in claim 1, in which the apparatus to be cleaned is (i) an activated carbon-filled reactor suitable for preparing phosgene from carbon monoxide and chlorine, or (ii) an activated carbon-filled reactor suitable for absorbing or decomposing phosgene in phosgene-containing gas streams, where the flow rate of gaseous ammonia which is guided through the activated carbon-filled reactor in step d) is in the range from 3 L/h to 30 L/h per metric ton of activated carbon.

8. The process as claimed in claim 7, in which step f) is followed by:
   g) removing the activated carbon and replacing it with fresh activated carbon.

9. The process as claimed in claim 1, in which the passing through of the inert gas stream from step c) is continued after completion of cooling of the apparatus to be cleaned.

10. The process as claimed in claim 9, in which the gaseous ammonia from an ammonia gas source is passed through in step d) by feeding it into the inert gas stream from step c).

11. The process as claimed in claim 9, in which an inert gas is passed through the apparatus to be cleaned in step e) solely by maintaining the inert gas stream from step c).

12. The process as claimed in claim 1, in which the apparatus to be cleaned is an activated carbon-filled reactor suitable for preparation of phosgene from carbon monoxide and chlorine.

13. The process as claimed in claim 12, in which the activated carbon-filled reactor suitable for preparation of phosgene from carbon monoxide and chlorine is part of a production plant for preparation of a chemical product by reaction of a phosgene-reactive starting material with phosgene.

14. The process as claimed in claim 13, in which the phosgene-reactive starting material is a compound having two or more phenolic hydroxyl groups or a compound having two or more primary amine groups.

15. The process as claimed in claim 13, in which the production plant for preparation of a chemical product has n independently controllable, activated carbon-filled reactors suitable for preparation of phosgene from carbon monoxide and chlorine, where n is a natural number from 2 to 5, where phosgene is prepared from carbon monoxide and chlorine in m reactors, where m is a natural number in the range from 1 to n−1, while cleaning steps a) to f) are conducted in at least one reactor.

\* \* \* \* \*